United States Patent
Klingenburg et al.

(10) Patent No.: US 11,395,722 B2
(45) Date of Patent: Jul. 26, 2022

(54) PARTIAL OR TOTAL PROSTHESIS

(71) Applicant: MERZ DENTAL GmbH, Lütjenburg (DE)

(72) Inventors: Friedhelm Klingenburg, Molfsee (DE); Carola Froelich, Ulm (DE)

(73) Assignee: MERZ DENTAL GmbH, Lütjenburg Schleswig-Holstein (DE)

( * ) Notice: Subject to any disclaimer, the term of this patent is extended or adjusted under 35 U.S.C. 154(b) by 0 days.

(21) Appl. No.: 16/998,323

(22) Filed: Aug. 20, 2020

(65) Prior Publication Data

US 2020/0390531 A1  Dec. 17, 2020

Related U.S. Application Data

(63) Continuation of application No. 15/867,443, filed on Jan. 10, 2018, now Pat. No. 10,779,916, which is a (Continued)

(30) Foreign Application Priority Data

Nov. 11, 2011  (DE) .......................... 102011118320.9

(51) Int. Cl.
*A61C 13/01* (2006.01)
*A61C 13/20* (2006.01)
(Continued)

(52) U.S. Cl.
CPC .......... *A61C 13/20* (2013.01); *A61C 13/0004* (2013.01); *A61C 13/0006* (2013.01);
(Continued)

(58) Field of Classification Search
CPC ..... A61C 13/20; A61C 13/01; A61C 13/0006; A61C 13/0022; A61C 13/0004; Y10T 29/49567
See application file for complete search history.

(56) References Cited

U.S. PATENT DOCUMENTS

| 3,846,911 A | 11/1974 | Wichner |
| 6,465,106 B1 | 10/2002 | Petticrew ............... A61C 13/20 428/426 |

(Continued)

FOREIGN PATENT DOCUMENTS

| DE | 40 25 728 | 2/1992 |
| DE | 10 2009 056 752 | 6/2011 |

(Continued)

OTHER PUBLICATIONS

European Office Action in Application No. 18198191.1, dated Apr. 17, 2019, 31 pages (With English Translation).
(Continued)

*Primary Examiner* — Rick K Chang
(74) *Attorney, Agent, or Firm* — Hueschen and Sage

(57) ABSTRACT

The invention relates to a milling block (1) for producing partial or total prostheses, comprising a prosthesis base (3) to be processed according to the shape of the jaw, on which synthetically moulded teeth (5), preferably a full set of teeth, are provided, a milling block system consisting of a first milling block for the upper set of teeth and a second milling block for the lower set of teeth, and a method for producing partial or total prostheses.

6 Claims, 2 Drawing Sheets

Figure 1:
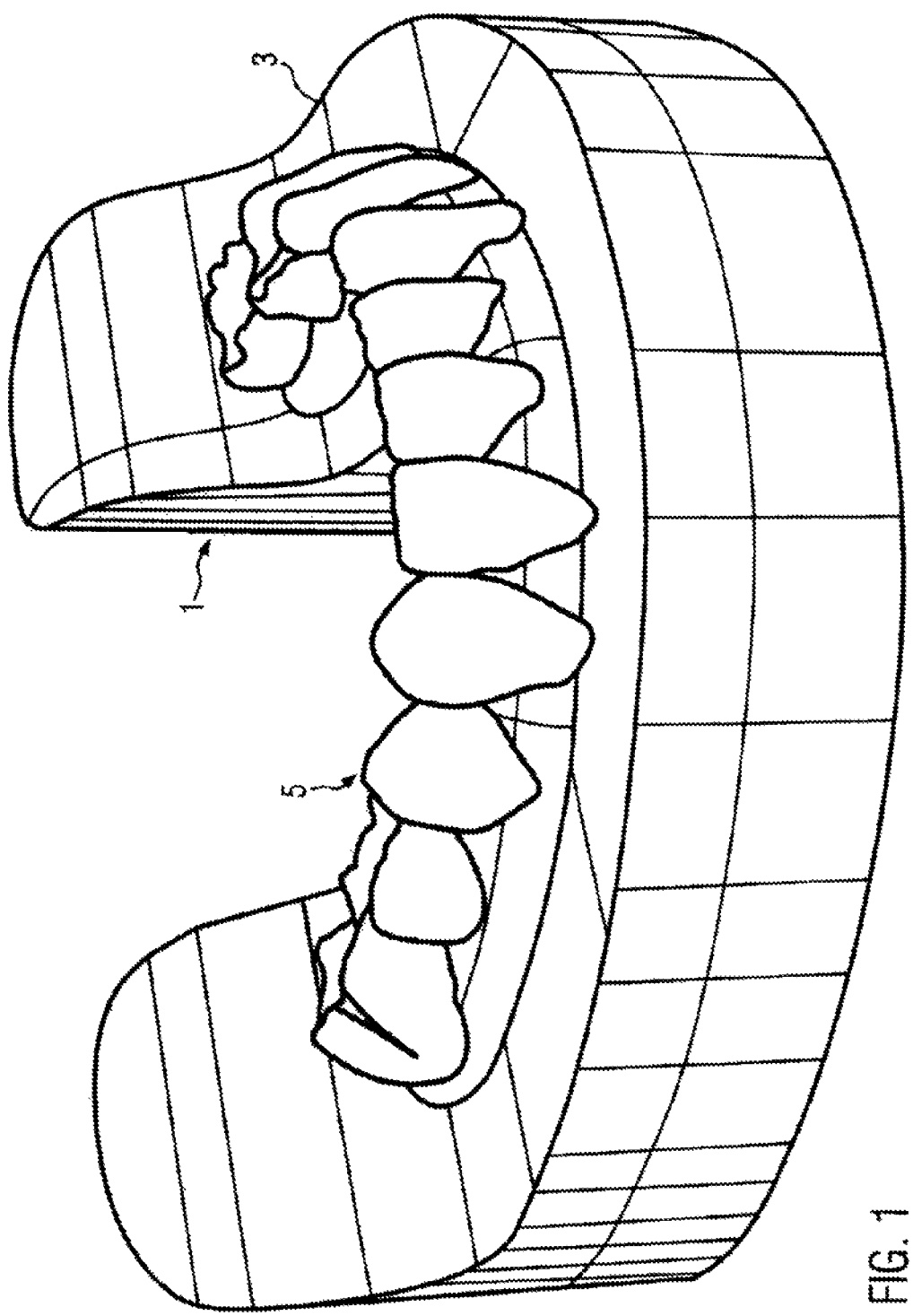

Related U.S. Application Data continuation of application No. 14/357,565, filed as application No. PCT/EP2012/004665 on Nov. 9, 2012, now abandoned.

(51) Int. Cl.
*A61C 13/00* (2006.01)
*G16H 20/40* (2018.01)

(52) U.S. Cl.
CPC .......... *A61C 13/0022* (2013.01); *A61C 13/01* (2013.01); *G16H 20/40* (2018.01); *Y10T 29/49567* (2015.01)

(56) References Cited

U.S. PATENT DOCUMENTS

| | | | | |
|---|---|---|---|---|
| 6,915,178 | B2 | 7/2005 | O'Brien | A61C 13/0004 700/118 |
| 8,262,388 | B2 * | 9/2012 | Dunne | A61B 5/4547 433/60 |
| 9,192,456 | B2 | 11/2015 | Howe | A61C 9/0053 |
| 2010/0086899 | A1 | 4/2010 | Holzner et al. | |
| 2012/0258430 | A1 | 10/2012 | Ruppert et al. | |
| 2017/0319313 | A1 | 11/2017 | Boehmert | |

FOREIGN PATENT DOCUMENTS

| | | |
|---|---|---|
| EP | 0 501 983 | 9/1992 |
| JP | H08-280712 | 10/1996 |
| JP | 2003-515429 | 5/2003 |
| RU | 2009136068 | 1/2010 |
| RU | 2433799 | 9/2010 |
| WO | 2010/057584 | 5/2010 |
| WO | 2011/066895 | 6/2011 |

OTHER PUBLICATIONS

U.S. Appl. No. 61/539,970, filed Sep. 27, 2011.
Russian Patent Office, Office Action for RU Application No. 2014123414 dated Jun. 30, 2015 (with English translation).
European Patent Office, International Search Report for PCT/EP2012/004665 dated Aug. 14, 2013 (with English translation).
Japanese Patent Office, Official Communication for Japanese Patent Application No. 204-540357 dated Aug. 9, 2016 (with English translation).
Japanese Patent Office, Official Communication for Japanese Patent Application No. 2014-540357 dated Apr. 4, 2017 (with English translation) .
Office Action in Japanese Application No. 2014-540357, dated Jan. 16, 2018.

* cited by examiner

PARTIAL OR TOTAL PROSTHESIS

The invention relates to a milling block, to a method for producing partial or total prostheses and to a complete milling block system consisting of a first milling block for the upper set of teeth and a second milling block for the lower set of teeth and to a method for providing a partial or total prosthesis.

A method for producing a total prosthesis with an upper and/or lower jaw base with the aid of a milling device is already known from EP 0 501 983 B1, the respective base being milled from a synthetic block and data on the oral cavity characterising the contour or topography being used. This method described therein also uses, after preparing the adapted base for the oral cavity, the further procedural step of positioning the required teeth in wax on the upper and/or lower jaw base, the prosthesis being completed by connecting the teeth to the base with the aid of a cold-curing polymer. Next the so-called reocclusion takes place so that the respective patient is provided with an optimal bite according to the latter's chewing movements.

This known method is therefore associated with the disadvantage that after completion of the upper and/or lower jaw base individual adaptation to the patient by appropriately positioning the teeth in wax is required, and this in turn makes the whole treatment sequence for the dentist and dental technician time-consuming and expensive.

It is therefore the object of the following invention to provide a milling block and a method for producing partial or total prostheses as well as a complete milling block system which avoid the disadvantages of the prior art. Furthermore, it is the object of the following invention to reduce the working steps for individual adaptation to the patient.

According to the invention it is proposed in order to achieve the objects to provide a milling block for producing partial or total prostheses wherein a prosthesis base with synthetically moulded teeth of a full set of teeth is provided that is to be processed according to the shape of the jaw. Within this context, the corresponding milling block system is also equipped as regards the upper set of teeth and the lower set of teeth independently of the fastening in the mouth.

With this measure according to the application it is made possible for only the prosthesis base to have to be milled or moulded, and with correct milling according to given CAD/CAM data on the oral cavity of the patient no further adaptation has to be made due to synthetically moulded teeth already anchored on the prosthesis base.

By appropriately optimised adaptation and adjustment of the prosthesis base to the oral cavity just one individual adaptation step is therefore required in order to provide for the patient optimally.

Due to the presence of a milling block or milling block system according to the application wherein there is an appropriate jaw shape for the prosthesis base to be processed with synthetically moulded teeth, one need neither take an impression of the bite in order to determine the maxillo-mandibular relationship nor undertake a time-consuming and expensive fitting.

With the measure according to the application subsequent insertion into an articulator to determine the positioning of the teeth is not therefore required because the synthetically moulded teeth are already prepared according to given basic data for the occlusion position.

According to the method according to the application for providing a partial or total prosthesis it is therefore possible that on the basis of the presence of upper and lower rows of teeth present in the form of the set of teeth in the occlusion position at least three different milling block systems in different proportions in the form of the set of teeth and size of the teeth can be provided in order to be able to provide for almost all patients. With this measure a time efficient and cost effective production method is achieved, and it is made possible for dentists and/or dental technicians to provide fully for the population in all countries.

Unlike the known dental prostheses and production methods for the latter the milling block according to the invention is based on a one-piece arrangement with a first region, which has a prosthesis base that can be processed according to the shape of the jaw, and a second region with a predetermined or standardised arrangement of synthetically moulded teeth or rows of teeth for upper or lower jaw sets of teeth. Therefore, as a preliminary stage for the dental prosthesis a milling block is provided which, in a particularly cost- and time-saving manner, can only be processed, i.e. milled, in its first region, namely the prosthesis base in order to be adapted to the shape of the jaw. The milling block system according to the invention comprises at least a first milling block for the upper set of teeth and a second milling block for the lower set of teeth, i.e. the preliminary stages of a partial or total prosthesis, which in the respective second region of the first and/or second milling block has a predetermined or standardised arrangement of synthetically moulded teeth or rows of teeth for the upper and lower jaw sets of teeth positioned according to established occlusion principles.

A majority of premouldings known from the prior art with different colours, sizes and shape combinations for the mucous membrane region and tooth region for the production of the dental prosthesis is considerably simplified with the present subject matter of the invention by the predetermined or standardised arrangement of synthetically moulded, polymerised in teeth or rows of teeth for the upper or lower jaw sets of teeth. According to the application it is advantageous that only the respective prosthesis base assigned to the mucous membrane region is to be milled.

Moreover, the predetermined or standardised arrangement of synthetically moulded teeth or rows of teeth for the upper and lower jaw sets of teeth positioned according to established occlusion principles are non-individualised, prefabricated dental prosthesis parts which do not require any further post-processing.

The predetermined or standardised arrangement of synthetically moulded teeth or rows of teeth for the upper and lower jaw sets of teeth positioned according to established occlusion principles takes place according to a selection of prefabricated dental prosthesis parts, i.e. synthetically moulded teeth or rows of teeth according to pre-specified and known positioning systems.

Other advantageous further developments of the invention are the subject matter of the sub-claims.

If, moreover, the synthetically moulded teeth and the prosthesis base are made in one piece, when producing the milling block a casting or pressing mould can almost be used which therefore also respectively uses just one material for the milling block which advantageously has both a smaller allergy potential and a higher bond strength.

If, advantageously, the milling block is configured in two parts, it is thus made possible for the first region, that is processed according to the shape of the jaw, to be produced in a standardised manner and to be joined to different teeth, likewise already positioned on a second region, which are of different sizes and have different factors. With the further development that the prosthesis base can be configured flexibly, simplified adaptation to the oral cavity and adaptation to the shape of the jaw of the respective patient can be allowed for.

Materials featured as particularly advantageous for the milling block and for the milling block system, i.e. the prosthesis base and/or teeth, are, among others, so-called PMMA plastics, as are also thermoplastics, organically and inorganically filled plastics and also low-allergy plastics. In addition, it is also advantageous to use any form of ceramic, in particular glass ceramics, leucite-reinforced ceramic, aluminium-reinforced ceramic, oxide ceramic, zirconium oxide ceramic, infiltration ceramic, feldspar ceramics, lithium disilicate ceramic. It is also conceivable to use materials that have been sintered, but that still require a further production step. The milling block or the milling block system can also be used with a combined dental prosthesis.

If the teeth are already aligned according to an occlusion position, total adaptation to the patient's oral cavity is therefore only undertaken by appropriately milling the prosthesis base. The patient can therefore be certain that with appropriate adaptation to the oral cavity or to the upper and lower jaw an optimal occlusion position is provided and so there is advantageously an unrestrictedly functional total prosthesis as regards the bite characteristics. Due to the milling block or milling block system according to the application and the corresponding method for producing partial or total prostheses it is possible, for example, to provide at least three different sizes with which a complete total prosthesis can be provided for almost every patient according to the shape of the patient's face and the size of the patient's oral cavity. Due to the simplicity of the adaptation of the total prosthesis the working steps for the adaptation to the oral cavity are therefore considerably reduced and so are also less expensive. Based on experience, with specific groups of the population the milling block system can also include just two types or more.

With regard to the preparation and positioning of the synthetically moulded teeth, with the milling block, milling block system according to the invention and the corresponding method all possible, previously known positioning systems for this purpose can be used, such as e.g. the so-called original positioning systems derived from Gysi, Gerber and Schreinemaker. Positioning systems according to APF and APF NT and TiF based on the Gysi and Gerber positioning techniques can also be used advantageously. According to Staub Cranial a mathematically calculating positioning technique is used which determines the original position of the teeth on the basis of measurements taken and accordingly positions again.

The milling block or the milling block system according to the application can also be used in particular for the production of partial prostheses if at the very least opposite quadrants of the upper or lower sets of teeth can be used. Due to the positioning prepared for the teeth in the occlusion position, after inserting in and adapting to the corresponding jaw region post-processing of the teeth is therefore also practically unnecessary.

One particularly advantageous production technique for the milling block or for the milling block system is the possibility of inserting the selected teeth, pre-polymerised, in the occlusion position in the first region of the prosthesis base and then only undertaking the final polymerisation upon joining to the second region of the prosthesis base. In this way it is made possible for the respective upper and lower jaw prosthesis to be prepared and produced in one piece and form- and force-fitted, and so it has a lower allergy potential and a higher bond strength.

Further embodiments of the present invention are the subject matter of the other sub-claims.

With the milling block or milling block system according to the application it is made possible for fixing or marking of any type for a zero position transfer or zero point transfer for the automatic CAD/CAM processing to be undertaken. This makes it possible to save a huge amount of time, in particular due to dispensing with scanning, in order to achieve the positioning and prevents defective processing in a CAD/CAM system.

The milling block and the milling block system according to the application and the method for producing partial or total prostheses are described below in examples by means of the drawings.

In FIG. 1 a milling block 1 is shown which has a prosthesis base 3 which is processed according to the shape of the jaw on which synthetically moulded teeth 5 of a full set of teeth are already provided. The synthetic teeth are already worked such that the teeth are aligned according to an occlusion position and so can interact optimally with the upper jaw (not shown). In this illustration, for example, the prosthesis base and the teeth are made in one piece, and so the production process has been simplified.

Figure 2:
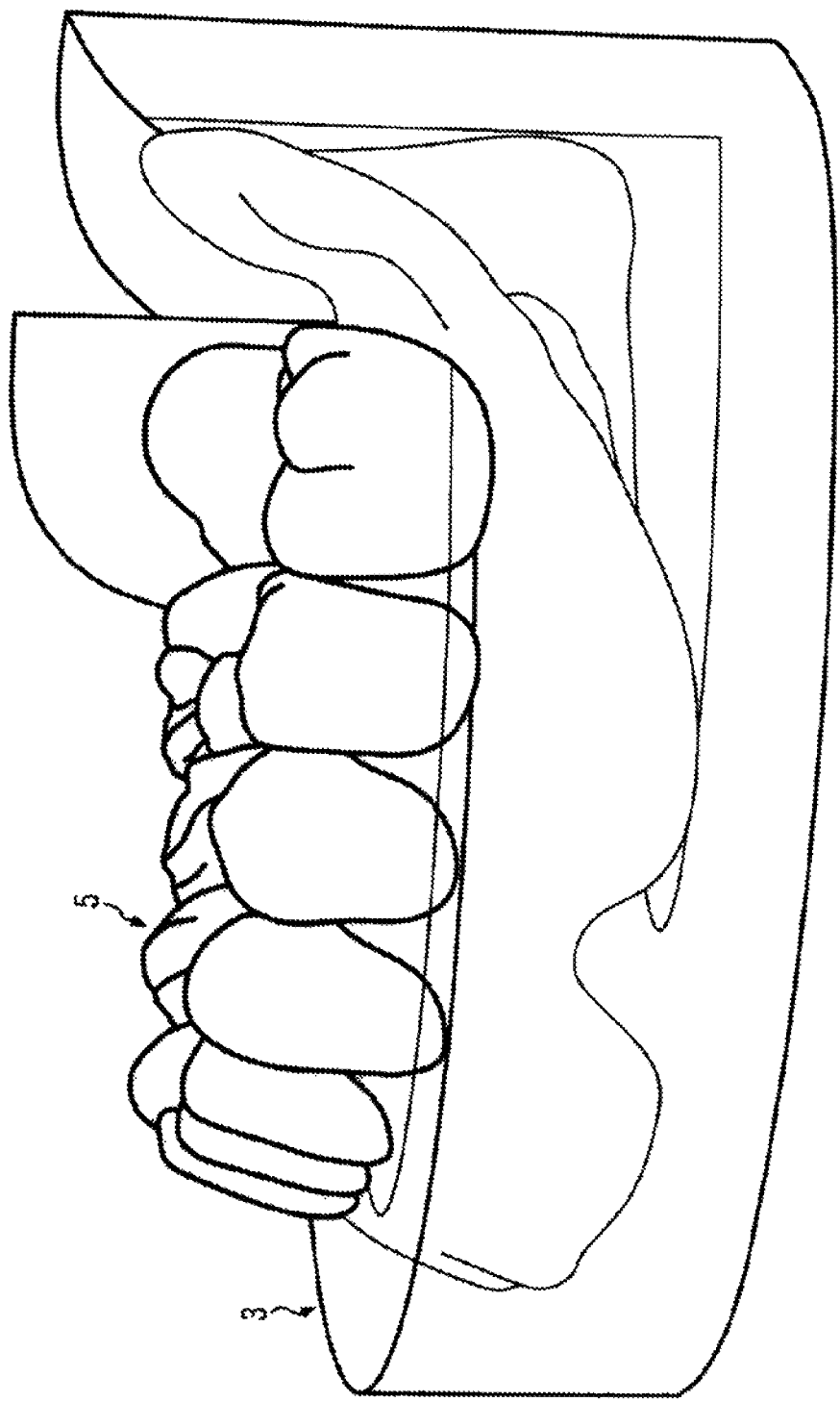

In FIG. 2 the completed total prosthesis of the lower jaw is shown, the prosthesis base 3 already being adapted to the oral cavity. FIG. 2 clearly shows how the shape of the oral cavity has been milled out of the prosthesis base, the teeth 5, which are aligned in the occlusion position, remaining untreated. It is thus made possible with the method according to the application that only by adapting the prosthesis base is there a complete total prosthesis the occlusion of which is coherent and does not necessitate any further procedural step, such as for example adaptation in an articulator. A further procedural step, as specified for example in the prior art, namely subsequent alignment by arranging the teeth in wax in order to achieve the occlusion position, is not necessary with the method according to the application.

The invention claimed is:

1. A partial or total dental prosthesis, the dental prosthesis comprising:
   synthetically molded teeth or rows of teeth integrally formed into a dental prosthesis base;
   wherein the dental prosthesis base is milled according to contour data of a patient oral cavity as defined by a mucous membrane surface of a patient jaw, thereby providing optimized adaptation and adjustment of the dental prosthesis base to the patient mucous membrane of the oral cavity; and
   wherein the synthetically molded teeth or rows of teeth are integrally formed into the dental prosthesis base according to established occlusion principles selected from a Gysi, Gerber, APF, APF NT, TiF, Schreinemaker, and/or Staub Cranial positioning method.

2. The partial or total dental prosthesis of claim 1, wherein the dental prosthesis base is milled from a ceramic selected from the group consisting of: glass ceramic, leucite-reinforced ceramic, aluminum-reinforced ceramic, oxide ceramic, zirconium oxide ceramic, infiltration ceramic, feldspar ceramics and lithium disilicate ceramic.

3. The partial or total dental prosthesis of claim 1, wherein the dental prosthesis base is milled from a material selected from the group consisting of: PMMA plastics, thermoplastics, PEEK nylon composite, organically and inorganically filled plastics, low-allergy plastics, out-burnable materials and sintered materials.

4. The partial or total dental prosthesis of claim 1, comprising an upper dental prosthesis and optionally a lower dental prosthesis, wherein the synthetic teeth are aligned according to established occlusion principles and are further positioned in dental prosthesis bases which have been milled according to contour data of the oral cavity of the patient defining a mucous membrane region.

5. The partial or total dental prosthesis of claim 1, wherein the dental prosthesis base conforms to the contour data of the oral cavity of the patient defining a mucous membrane region according to CAD/CAM data.

6. The partial or total dental prosthesis of claim 1, wherein the synthetically molded teeth are integrally formed into the dental prosthesis base by polymerization, by adhesive bonding, by pressing and/or melting together.

\* \* \* \* \*